United States Patent [19]

Klosa et al.

[11] Patent Number: 4,742,065
[45] Date of Patent: May 3, 1988

[54] SALTS OF BASIC CAFFEINE-8-ETHERS AND THEIR USE AS PHARMACEUTICALS

[75] Inventors: Josef Klosa; Hans Kröger, both of Berlin, Fed. Rep. of Germany

[73] Assignee: Sanorania Dr. G. Strohscheer, Berlin, Fed. Rep. of Germany

[21] Appl. No.: 707,488

[22] Filed: Mar. 1, 1985

[51] Int. Cl.$^4$ .................... C07D 473/08; A61K 31/52
[52] U.S. Cl. .................... 544/273; 544/266; 544/267
[58] Field of Search .................... 544/266, 273, 267; 514/267

[56] References Cited

FOREIGN PATENT DOCUMENTS 3232883  3/1984  Fed. Rep. of Germany .

OTHER PUBLICATIONS

Wyngaardene et al., Textbook of Medicine pp. 2267-2268 (1983).

Conn's Current Therapy pp. 672-675 (1984).

Primary Examiner—Nicholas S. Rizzo
Attorney, Agent, or Firm—Cushman, Darby & Cushman

[57] ABSTRACT

Salts of basic caffeine-8-ethers having the following general formula are disclosed:

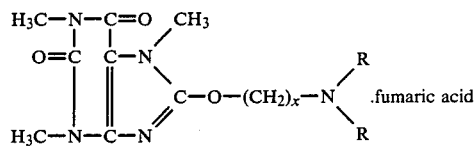

where X=2 or 3 and R is an alkyl group having from 1 to 3 carbon atoms, whereby the chain may be branched, in the form of fumarates. The components have pharmaceutical properties including effectiveness as antipsoriatics.

7 Claims, No Drawings

SALTS OF BASIC CAFFEINE-8-ETHERS AND THEIR USE AS PHARMACEUTICALS

The invention relates to novel salts of basic caffeine-8-ethers of the following formula

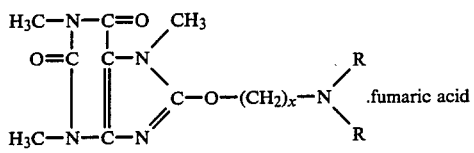

in which x=2 or 3 and R represents an alkyl group with 1 to 3 C atoms whereby the chain may also be branched, in the form of fumarates, and their use as pharmaceuticals, especially as anti-psoriatics.

It has been found that basic caffeine-8-ethers of the given constitution can be reacted with fumaric acid in a molar ratio of 1:1 to form stable fumarates which crystallize well. The hydrochlorides of the above-mentioned basic caffeine-8-ethers are known but these salts are of poor stability. They are hygroscopic and therefore not very suitable for use in pharmaceutical compositions. The free bases of the caffeine-8-ethers are easily soluble in water. Their aqueous solutions react basic (pH 9-10) and are easily hydrolyzed upon heating to form 8-hydroxy-caffeine. This is a further reason for the limited use of the basic caffeine-8-ethers as active agent in pharmaceutical specialties.

It has now been found that the fumarates of the basic caffeine-8-ethers have unlimited stability, crystallize well as salts, dissolve in water with neutral reaction, and that their solutions in boiling water do not undergo a cleavage to 8-hydroxy caffeine. They are stable.

It has further been found that they possess a special effect as anti-psoriatic. In solutions, ointments or the conventional application forms for external use solutions comprising 0.5 to 5, especially 2% by weight of 8-[(3',3'-dimethylamino propoxy)caffeine]-fumarate exhibit a beneficial effect against psoriasis. Such effect is surprising and could not be predicted.

Psoriasis is considered an uncurable skin disease for the cause of which there exists a great number of theories, and many compounds have been proposed for its treatment, including fumaric acid itself and its esters in relatively high concentrations up to 20% in combination with zinc salts, copper salts, iron salts and/or calcium salts (compare British patent specification No. 2,530,372), and finally in combination with amino acids such as cysteine or methionine, and with vitamin C.

In all these and other cases combinations with fumaric acid are involved but in no case a defined salt of fumaric acid with organic bases since it was feared that at the high dosage of fumaraic acid required for the external treatment of the affected skin the proportion of basic component would have undesirable effects on the wellbeing of the person afflicted by psoriasis. A detailed review on the present therapy of psoriasis has been published in "Arzneimittelbrief", June 1981, No. 6 (1981), page 61. Fumaric acid as remedy against psoriasis is not even mentioned in this critical review.

Symptoms resembling psoriasis cannot be produced in animal tests. Accordingly the activity of compounds which could be effected against psoriasis cannot be observed and reproduced.

The efficacy of a novel compound against psoriasis can accordingly only be judged by applying it directly to humans, especially in cases which have sofar been treated unsuccessfully. Such compound must also in itself be nontoxic, should have a certain relation to the body compounds and should be well compatible with the skin.

The group of compounds according to the invention meets these requirements. In a number of therapy-resistent cases of psoriasis it has been found that 8-[(3',3'-dimethyl amino propoxy)-caffeine]-monofumarate not only gives an excellent cosmetic effect but exhibits a beneficial effect against psoriasis. Sufficient beneficial effect effect was obtained within 14 days without relapse during two years so that the treatment can be considered fully satisfactory.

The preparation of the novel salts of basic caffeine-8-ethers is carried out by reacting 8-(dialkylamino alkyl)-caffeines with fumaric acid in a molar ratio in suitable solvents and diluents, especially lower alkanols like methanol, ethanol or isopropanol, and dilution of the reaction mixture with ketones such as acetone or with ethers like diethyl ether. The novel salts will either directly crystallize from the solutions or they can be precipitated from their solutions with acetone or diethyl ether.

The novel salts of the invention are soluble in water. Suitable 8-(dialkylamino alkoxy)-caffeines for the salt formation are the following:
8-(3',3'-dimethylamino propoxy)-caffeine
8-(2',2'-dimethylamino ethoxy)-caffeine
8-(2',2'-diethylamino ethoxy)-caffeine
8-(2',2'-diisopropylamino ethoxy)-caffeine The 8-[(3',3'-dimethylamino propoxy)-caffeine]-fumarate will below referred to in short as Cofpsoron.

The compounds of the invention can be applied in alcoholic lotions, in ointments, gels, baths and in suitable diluents for the external treatment of psoriasis or also in the form of tablets, coated tablets, drinks, juices for the internal application or in ampoules for injection purposes.

A suitable dosage form for the external local application is a concentration of e.g. 0.5 to 5% Cofpsoron, in tablets or the like for internal intake doses of 10 to 200 mg, especially of 50 to 100 mg and for injections 50 to 250 mg pro ampoule.

The following examples illustrate the invention without limiting the invention thereto.

EXAMPLE 1: PREPARATION OF THE FUMARATES (a) 26 g of 8-(3',3'-dimethylamino propoxy)-caffeine were dissolved in 200 ml ethanol. Approximately 12 g of fumaric acid were added to this solution. The fumaric acid was completely dissolved. Thereafter the mixture was heated on a water bath to 50°-60° C. The solution was filtered (plaited filter) and diluted with 200 ml of acetone, after a short time for the fumarate crystalized from the solution. Fp. 170°-172° C. sharp, the melt is colorless. Yield: 35 g.

(b) 12 g fumaric acid were dissolved under heating in 200 ml methanol. A solution of 26 g 8-(3',3'-dimethylamino propoxy)-caffeine in 60 ml methanol was added to the first solution. The mixture was heated for 15 to 30 minutes on a water bath to 50° to 60° C., optionally filtered, and 100 ml of acetone and 50 ml of diethyl ether were added to the clear solution. The fumarate crystallized in coarse crystals. Fp. 170°–172° C. Yield: about 36 g.

The following were prepared in the same manner:
8-[(2',2'-dimethylamino ethoxy)-caffeine]-fumarate
8-[(2',2'-diethylamino ethoxy)-caffeine]-fumarate
8-[(2',2'-diisopropylamino ethoxy)caffeine]-fumarate 1 g of the fumarates thus obtained can be dissolved at ambient temperature in 5 ml of water. The fumarates are easily soluble in lower alcohols, insoluble in ketones such as acetone, insoluble in ether and in benzene hydrocarbons.

EXAMPLE 2: GALENIC COMPOSITIONS (a) Lotions 20 g of 8-[(2',2'-dimethylamino propoxy)-caffeine]-fumarate (Cofpsoron) were dissolved in 150 ml of water. This solution was added to the following solution:
600 ml isopropanol
8 ml lavender oil
6 ml ol. pini
4 ml melissa oil
10 ml isopropyl palmitate
20 ml polyethylene glycol 200

The solution should be clear and is diluted with water to 1000 ml; if the solutions becomes turbid due to precipitation of the etherial oils the water is replaced by isopropanol.

(b) Ointments
Cofpsoron according to example 1: 15 g
Ointment base ad: 1000 g (c) Bath Oils
Cofpsoron according to example 1: 10 g
Thistle oil: 750 ml
Lavender oil: 60 ml
Bergamot oil: 40 ml
Rosemary oil: 30 ml
Trilon 100: 10 ml
Trilon 101: 10 ml
Isopropanol ad: 1000 ml

| (d) Capsules | |
|---|---|
| Cofpsoron according to example 1 | 100 mg |
| Lactose | 80 mg |
| Avicel pH - 102 | 20 mg |
| Aerosil - 200 | 1 mg |
| Magnesium stearate | 2 mg |
| Weight of the capsule | 200 g |

EXAMPLE 3: APPLICATION AS PHARMACEUTICAL COMPOSITION (a) Angela R. born 1935, suffering since 1958 from arthritic psoriasis vulgaris, skin areas with scale formation about 5×8 cm.

Prior treatment: Tar compositions, zinc oxide ointments, 10% salicylic acid compositions, corticosteroids, Dithranol (Cignolin). The treatment was unsuccessful. In March 1982 a Cofpsoron lotion according to example 2a was applied daily during 14 days. A clear improvement was observed; the treatment was interrupted for three weeks in order to observe whether the improvement persisted. It did persist, and Cofpsoron was again applied for 8 days. The symptoms disappeared completely. The effect persisted so that this case can be considered successfully treated.

(b) Erich G., born 1911, scale formation in large areas on the lower arms since 1917, i.e. as a boy. Treatment was attempted with alumina acetate following medical prescription—without success. Red spots and scale formation occurred later on other body parts, persistent on the head. Treatment was attempted according to the present status of therapy with different ointments, internally with arsenic tincture and a diet. Success was small.

The test person reported that especially eating of cheese resulted in a catastrophic increase of the skin psoriasis and especially formation of scale in the hear bearing areas on the head. The therapy with recent drugs like Psoralm and with irradiation as well as with retinoids resulted in little improvement. According to the opinion of the test person dietectic measures showed better results so that he became non-smoker and non-alcoholic and subjected himself periodically to a strict diet. In spite of the various therapeutic attempts during several decades the psoriasis persisted on his head. Since January 1982 Cofsporon has been applied daily. After three weeks of treatment the scaly islands disappeared.

(c) Three further untreatable psoriasis cases were treated in the same manner with apparent success using the Cofpsoron lotion of example 2a.

Remark: In all five cases the test persons suffered from a disease resisting all therapeutic attempts; the disease made the life of the test persons miserable, sometimes over decades. The observed effects were not transitory as is often the case in the treatment of psoriasis but the beneficial effects persisted so that it can be concluded that a fully satisfactory result has been achieved.

We claim:

1. Caffeine-8-ether monofumarate compounds selected from the group consisting of compounds of the formula $$\begin{array}{c} H_3C-N-C=O \\ | \quad | \\ O=C-C-N \\ | \quad | \\ H_3C-N-C-N \end{array} \begin{array}{c} CH_3 \\ \diagup \\ \\ C-O-(CH_2)_x-N \diagup R \\ \diagdown R \end{array} \cdot \text{Fumaric Acid}$$

wherein X=2 or 3 and R represents an alkyl group of 1 to 3 carbon atoms.

2. Monofumarate compound as claimed in claim 1, wherein said caffeine-8-ether compound is a member of the group consisting of
8-(3',3'-dimethylamino propoxy)-caffeine,
8-(2',2'-dimethylamino ethoxy)-caffeine,
8-(2',2'-diethylamino ethoxy)-caffeine, and
8-(2',2'-diisopropylamino ethoxy)-caffeine.

3. Chemical compound for the treatment of psoriasis consisting essentially of 8-[3',3'-dimethylamino propoxy)-caffeine]-monofumarate.

4. Method of preparing the caffeine-8-ether monofumarate compounds claimed in claim 1, said method comprising (a) mixing a caffeine-8-ether compound of the formula $$\begin{array}{c} H_3C-N-C=O \\ | \quad | \\ O=C-C-N \\ | \quad | \\ H_3C-N-C-N \end{array} \begin{array}{c} CH_3 \\ \diagup \\ \\ C-O-(CH_2)_x-N \diagup R \\ \diagdown R \end{array}$$

where X is 1 or 2 and where R represents an alkyl group of 1 to 3 carbon atoms, with a lower alkanol solvent;

(b) adding to said mixture a quantity of fumaric acid equimolar with said caffeine-8-ether compound to form a solution of said caffeine-8-ether monofumarate.

5. Method according to claim 4 further comprising the step of diluting said solution of caffeine-8-ether monofumarate with acetone, thereby causing crystallization of said monofumarate compound.

6. Method according to claim 4 further comprising the step of diluting said solution of caffeine-8-ether monofumarate with diethyl ether, thereby causing crystallization of said monofumarate compound.

7. Method according to claim 4 wherein said solvent is selected from the group consisting of methanol, ethanol and isopropanol.

* * * * *